United States Patent [19]

Wade

[11] Patent Number: 4,594,326

[45] Date of Patent: Jun. 10, 1986

[54] TIME-INTEGRATED MEASUREMENT FOR DETERMINING SUBSTANCES IN BIOLOGICAL FLUIDS

[76] Inventor: Stephen E. Wade, 3611 Guion Rd., Apt. D, Indianapolis, Ind. 46222

[21] Appl. No.: 492,705

[22] Filed: May 9, 1983

[51] Int. Cl.$^4$ .......................................... G01N 33/50
[52] U.S. Cl. ................... 436/501; 128/632; 128/633; 128/635; 128/637; 128/768; 422/68; 436/52; 436/514; 604/892
[58] Field of Search ............... 604/892; 128/632, 633, 128/635, 637, 768; 436/501, 52, 514; 422/68

[56] References Cited

U.S. PATENT DOCUMENTS

| | | | |
|---|---|---|---|
| 3,518,982 | 7/1970 | Timmins | 128/632 |
| 3,993,072 | 11/1976 | Zaffaroni | 604/892 |
| 4,016,864 | 4/1977 | Sielaff | 128/632 |
| 4,220,152 | 9/1980 | Dresback | 604/892 |
| 4,325,388 | 4/1982 | Bucalo | 128/768 |

OTHER PUBLICATIONS

Chemical Abstracts, 89:211544f (1978).
Joseph W. Goldzieher et al., Journal of Clinical Endocrinology and Metabolism, 43:824 (1976).
Zakik et al., Journal of Clinical Endocrinology and Metabolism, 51:1099 (1980).
Lasnitzki and Franklin, Journal of Clinical Endocrinology and Metabolism, 64:289 (1975).
A. Vermeulen et al., Journal of Clinical Endocrinology and Metabolism, 33:759 (1971).
A. Kowarski et al., Journal of Clinical Endocrinology and Metabolism, 32:356 (1971).
Schellman et al., Journal of the American Chemical Society, 76:2808 (1954).
Seal and Doe, Steroids, 5:827 (1965).
Ballard et al., Journal of Clinical Endocrinology and Metabolism, 41:290 (1975).
P. G. Goode, British Journal of Pharmacology, 41:558 (1971).
Cheesman et al., Fertility and Sterility, 38:475 (1982).

Primary Examiner—Sidney Marantz
Attorney, Agent, or Firm—O'Rourke & Harris

[57] ABSTRACT

A method for obtaining a measurement of the time integral of concentrations of substances in a biological fluid, without the necessity to collect samples of that fluid, and a device useful in the practice of that method. The concepts accomplish time-integrated measurement of the freely-diffusable fraction of substances of interest by providing conditions under which the rate of accumulation of such substances by a device placed in intimate contact with the biological fluid is at all times proportional to their concentration.

9 Claims, 3 Drawing Figures

U.S. Patent  Jun. 10, 1986  4,594,326
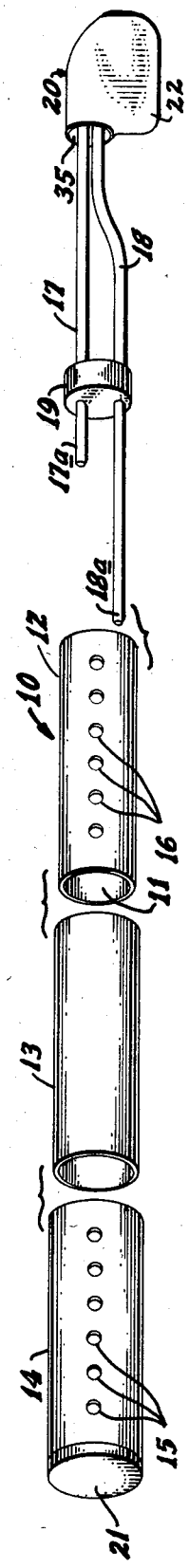
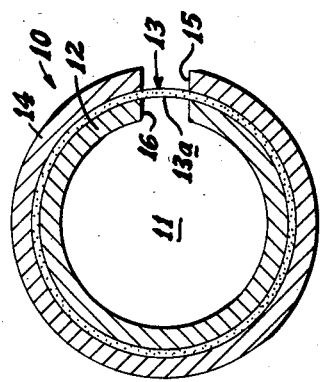
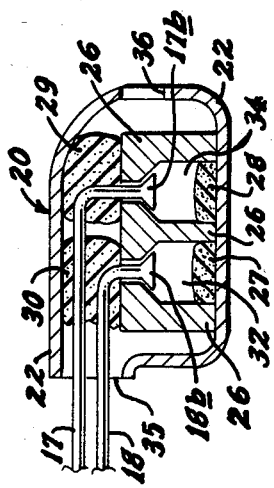

TIME-INTEGRATED MEASUREMENT FOR DETERMINING SUBSTANCES IN BIOLOGICAL FLUIDS

BACKGROUND OF THE INVENTION

1. Field of the invention:

This invention relates to a method for obtaining an estimate of the time integral (defined below) of the concentration of a substance in a biological fluid.

More particularly, it relates to a method for obtaining, for assay, a single aliquot of material, in which the content of the substance of interest provides a direct measure of the time integral of the concentration of the freely-diffusable fraction of that substance in the biological fluid over a known time interval; and the invention also provides a device useful in the practice of this method.

2. Nature and significance of time-integrated measurement of biochemical substances:

Very often a primary goal in making measurements of substances in biological fluids is to provide information about some enduring state of the organism which produces those fluids, such as when biochemical measures are taken to provide information for the diagnosis of disease.

It often happens that the concentrations of these substances in the biological fluids are subject to temporal fluctuations, such that a series of samples taken from the biological fluids would reveal a distribution of concentration values. Generally it is not the concentration present at a given instant, but rather the extended summation of the fluctating concentrations over some time interval, which is of ultimate interest. This summation of instantaneous levels over a defined time interval, in mathematical terms, would be called the "time-integral".

The time-integral is preferred because it is more representative of the enduring state of the organism than are the temporally-fluctuating instantaneous values. The time integral, divided by the length of the time interval over which it was obtained, is equivalent to the true average concentration of the substance over that interval.

This advantage of the time-integral over instantaneous values is illustrated by Goldzieher et al. (*Journal of Clinical Endocrinology and Metabolism* 43:824 (1976)). These authorities estimated the 8-hour mean of blood plasma luteinizing hormone concentrations in normal men by a prior art method (described below), then calculated the probability that a single plasma sample would yield a value within plus or minus 20 percent of this mean.

They estimated this probability was only 30%, i.e., that a single plasma measurement was a very poor indicator of the enduring state of the organism, with regard to this important substance.

The practical diagnostic advantage of time-integrated measurement can be illustrated by another example from the medical literature. Zadik et al. (*Journal of Clinical Endocrinology and Metabolism* 51:1099, (1980)) compared the ability of three clinical tests to distinguish among the three classes, i.e., normal persons, patients with mild essential hypertension, and patients with Cushing's syndrome. Three tests were used for each of those three classes of patients: (1) a prior-art method (described below) of estimating the time integral of plasma cortisol, (2) measurement of urinary free cortisol, and (3) measurement of urinary 17-hydroxycorticosteroids. The latter two methods are recognized to be far superior to instantaneous plasma cortisol measurement, and are considered to be the standard measures in current medical practice.

However, the time-integrated plasma cortisol measurement was found to be clearly superior to the standard measures in discriminating among these groups. The authors nevertheless declined to recommend the time-integrated measurement as a new standard of practice, however, because the prior art heretofore available for that improved method is exceedingly complex.

3. Nature and significance of measurement of the "free" fraction of biochemical substances:

It often happens that compounds of biological interest (e.g., hormones, drugs, amino acids, etc.) exist in biological fluids in two states or fractions, i.e., those molecules which are in association with macromolecules (generally proteins) such that their movements and reactions are in some way limited by the macromolecules, and those which are free of such association.

The latter fraction is often called the "free" fraction, and the former the "bound" fraction; and in general, the proportion of the bound and free fractions is determined by the concentrations of the various biochemical components of the biological fluid, by temperature, and by other factors of a physical or chemical nature.

When the compounds of interest exist in both "bound" and "free" states, it is often observed that the biological effects of the compounds seem to be exerted only by the free fraction (see for example Lasnitzki and Frankin, *Journal of Endocrinology* 64:289, (1975)).

Indeed, it is found that the free fraction concentration of a hormone in a biological fluid is a much better indicator of the state of the organism than is the total concentration. Vermeulen et al. (*Journal of Endocrinology and Metabolism* 33:758, (1971)) present many cases illustrating the superiority of measurements of free testosterone concentration obtained by a prior art method (described below), over simple measurement of the total hormone concentration, again in the context of medical diagnosis.

DESCRIPTION OF THE PRIOR ART a. Prior art of measurement of the time-integral of substances in biological fluids:

Essentially, the prior art as to the measurement of the time-integral of substances in biological fluids consists of two similar methods. As now described, they are seen to both fail to achieve the advantageous non-restrictive procedure of the present invention; and, instead, both require the removal of samples or specimens over a prolonged time period, and other differences as noted herein.

The method described by Kowarski et al. (*Journal Clinical Endocrinology and Metabolism* 32:356, (1971)) is typical of those using a prolonged sample-removal procedure, this type being a constant-withdrawal system (U.S. Pat. No. 3,908,657) to obtain a sample.

In this Kowarski method, a mechanical pump is used to obtain a sample of the biological fluid at a constant rate over a long time interval. The content of the relevant substance in the sample is then measured by suitable means; and since each instant of the elapsed interval is represented by an equal amount of fluid in the sample, the concentration of the compound of interest in the whole sample directly reflects the time integral of its concentration in the biological fluid over the pumping interval. This is similar to the method employed by Zadik, et al. (1980).

In practice, this method has several disadvantages, relative to the invention to be described here; and the disadvantages of this prior art method are now summarized.

First, the continuous removal prior art method of Kowarski involves the use of a miniaturized precision pump which is very expensive to manufacture, relative to the device of the invention to be described.

Second, a very bothersome disadvantage is that a specially-treated catheter must be inserted in a major blood vessel of the subject, and maintained without thrombosis for the duration of the measurement procedure; this requirement makes the method stressful for some if not most subjects and even impossible for others (such as some animals which will not tolerate the externalized catheter connection).

Third, the continuing sample-removal procedure of the prior art has the disadvantage that the necessity to avoid thrombosis in the catheter places limits on the slowness with which blood can be withdrawn, and places limits upon the duration of the sampling period; and these limits are so restrictive that small animals (such as laboratory rats) are not suitable subjects due to their limited blood volume, and most subjects cannot reliably be monitored for more than 24 hours without changing catheters.

Fourth, as a disadvantage, and even if the other obvious bothers and distress to the subject were not present, the subject must either be severely limited in its movements, or else must carry the pump and associated apparatus along with it by some means.

Fifth, this prior art method has been applied only to blood.

The second prior art method, also of prolonged sample-removal nature, is typified by the method of Goldzieher, et al. (1976). In that method, multiple instantaneous samples are obtained frequently and at regular intervals throughout the measurement period. The concentration of the compound of interest is measured by suitable means in each sample, and the results are then mathematically integrated to yield an estimate of the time intregral.

That prior art method, because it too is of course of prolonged sample-removal type even though of repetitive rather than continuous nature, shares many disadvantages with the previously-described prior art, and is generally more laborious, as will be apparent when it is considered that either a catheter must be maintained as before, or repeated blood samples otherwise drawn, and that a large number of samples of the blood plasma must be measured by suitable means, thus more disadvantageous in this respect than in the former prior art method in which a single pooled sample was involved.

b. Prior art of measurement of the free fraction of biochemical substances:

The prior art as to measurement of the free fraction of biochemical substances consists of a number of methods for accomplishing a physical separation of the macromolecules which bind the compounds of interest, from some remaining part of the sample, without seriously disturbing the proportion of the bound and free fractions. All such prior art methods fail to provide advantages of the present invention, in that they require further procedures in addition to that of an already-complex analysis.

Among the oldest methods is equilibrium dialysis, as shown in Schellman et al., *Journal of the American Chemical Society* 76:2808 (1954), in which is used a membrane which permits the passage of the free compound of interest, but not the macromolecules and the associated bound compound. The membrane is arranged so that it serves as a differentially-permeable barrier between the sample with its bound and free fractions, and a small volume of a similar fluid, which contains neither the macromolecules nor the bound or free portions of the compound of interest.

With this type of device, substances which can pass through the membrane do so in accordance with the laws of diffusion; and eventually an equilibrium is reached wherein the concentration of the "free" compound of interest is equal on both sides of the membrane, while the macromolecules on the "sample" side of the membrane continue to sequester the "bound" fraction.

The small volume containing only "free" compound is then removed and the total concentration therein measured by suitable means, thus yielding an estimate of "free" compound concentration in the original sample.

Other methods in the prior art accomplish the separation of macromolecules by causing them to be insoluble in the fluid without causing them to release the "bound" molecules. The means for making the macromolecules insoluble differ from one case to another, but generally involve the introduction of chemical species which combine with the macromolecules to produce an insoluble complex, which is an additional step not required by the present invention.

SUMMARY OF THE INVENTION

1. Achievements of the invention:

The general achievement of the present invention is the provision of a novel means and method for obtaining a measurement of the time integral of the concentration of a biochemical substance in a biological fluid, and a novel device useful therefor.

A more particular achievement of the present invention is the provision of such a method and device such that the measurement is confined to the time integral of the concentration of the "free fraction" of the biochemical substance, as previously defined.

A further achievement is the provision of such a method and device which does not require the collection of blood, and which is not limited in application to blood plasma.

Another achievement is the provision of such a method and device which produces a single aliquot of material in which the content of the substance of interest, when measured by suitable means, is a direct measure of the time integral of the free fraction of the said substance in the biological fluid, over a known time interval.

Still another achievement is the provision of such a method and device which are adapted to repeated measurements of that time integral within a single subject, as may be desired or required in some experimental procedures.

Yet another achievement is the provision of such a method which can be used to measure the said time integral over long or short periods of time, and in subjects which are free of any external restraint or encumberance.

A further achievement is the provision of such a method and device which are adaptable to the measurement of that time intregral of a great variety of biochemical substances.

A still further achievement is the provision of such a method and device which can, by virtue of the cumulative nature of their operation, allow the measurement of the time integral of substances, which at any one instant are at such low concentration in the biological fluid as to be unmeasurable by present methods.

2. The drawings, operative principles, and a desirable embodiment:

These and other objects, features, and advantages will be apparent from the following description of the presently-preferred embodiment of the invention, taken in conjunction with the accompanying generally schematic drawings of a device useful in the practice thereof, and in which:

FIG. 1 is a pictorial, generally exploded view of a device of the present invention, and which is useful in the implementation of the method according to the inventive concepts;

FIG. 2 is a longitudinal sectional view, in larger scale, of the external-connector portion of the device shown in FIG. 1, showing details of its construction;

FIG. 3 is a transverse cross-sectional view through the main body of the device, showing the arrangement of the three layers of the device's construction, but with its components no longer in the exploded-view condition.

Part of the invention is the discovery that when a fluid containing certain substances capable of binding the substances of interest is contained within a device, which is constructed so as to allow diffusion of the substances of interest in their "free" form from outside the device to inside at a precisely-controlled rate, yet able to contain these certain substances capable of binding the substance of interest within the device, and when such a device containing such a fluid is installed in intimate contact with the biological fluid, with a means provided for recovering the contents of the device after some time has elapsed, and the content of the substance of interest present at that time in the recovered fluid is measured by suitable means, that the several advantageous achievements of the present invention are realized.

The method of the invention and the device found useful in the practice thereof will be explained using as an illustrative example the particular case of an embodiment of the invention presently preferred for measuring the time integral of the free fraction of the hormone corticosterone, in the interstitial fluid of laboratory rats.

However, it will be understood that many modifications of particulars of the embodiment preferred for this purpose may be made, without departing from the novel concepts of this invention.

Illustrative of some modifications which are preferred when the invention is used for other purposes, are set forth herein also, so that it will be readily understood how all the objects and attainments of the invention are achieved by modifications within these concepts herein set forth.

The present invention involves the creation and maintainance of conditions within an implanted device, such that the rate of diffusion of the free fraction of the compound of interest from the body fluids surrounding the implanted device, into the device itself, is a known function of the concentration of the free fraction of that compound in the body fluid which is in intimate contact with the device.

These conditions are created and maintained by providing, as the inside of the implanted device, a fluid-filled compartment in which the concentration of the free fraction of the compound of interest is maintained at a very small value relative to its concentration outside the device.

This interior fluid-filled compartment communicates with the biological fluid in which the implant resides, across a layer of material which provides a pathway of known and constant permittivity for the diffusion of the compound of interest in its free form, but which is essentially impermeable to macromolecule-bound forms and to macromolecules in general.

The arrangement of these features will be more apparent by reference to the device 10 as shown in FIG. 3, in which the interior fluid-filled compartment 11 communicates with the device's immediate environment through the differentially-permeable membrane 13, which is held in place between the compartment 11 and the environment by virtue of its juxtaposition between rigid shell 12 and outer shell 14, and which comprises the only barrier to free transfer of material between the compartment 11 and the environment in the region defined by a row of apertures 15 in shell 14 and a corresponding row of apertures 16 in the shell 12.

The region 13a defined by one set of corresponding apertures 15 and 16 in which membrane 13 is exposed will hereafter be referred to as a "diffusion port"; and it will be noted that the apertures 15 and 16 of the two rows are correspondingly spaced along each row, and that corresponding ones of each of the apertures 15 and 16 are in registry when the shells 12 and 14 are in assembled condition.

When components 12, 13 and 14 are assembled, in contrast to their "exploded-view" showing in FIG. 1, the device 10 provides a sealed compartment 11 having multiple diffusion ports 13a, each like the one shown in FIG. 3 and with a means provided for recovering the contents of the sealed compartment 11 without removing it from the animal, as is more further described below.

The means of maintaining the concentration of the free compounds of interest at a very small value, as indicated above as being required, will differ depending upon the compound to be measured; but in general this requirement is met by providing a solution or suspension of a protein which is able to form a high-affinity complex with the compound of interest, such that the complexed form is not available for diffusion across the differentially-permeable membrane.

In the illustrative case of corticosterone, many such proteins are known in the related arts, including but not limited to plasma corticosteroid binding globulins (Seal and Doe, *Steroids* 5:827 (1965)), immunoglobins having affinity for corticosterone, and corticosteroid receptor proteins (Ballard et al., *J. Clin. Endo. Metab.* 41:290 (1975)).

In the presently preferred embodiment of the invention, there is used blood serum of rats, which contains rat corticosteroid binding globulin and from which endogenous steroids have been removed by incubation with charcoal.

The choice of the binding preparation is a matter of convenience among preparations having the desired binding property, and the use of another binding preparation, including even a non-protein binder, is not outside the novel concepts of this invention.

The binding preparation is used to maintain the concentration of the free fraction of the compound of interest inside the device at a low value relative to its concentration in the environment of the device, as required above. A low value is recognized as one which does not result in significant reduction in the rate of diffusion across the differentially-permeable membrane, when the environmental concentration of the free fraction is at its minimal expected value, compared to the rate which would exist if the concentration inside the device were zero.

Recognition of what constitutes a low value thus requires knowledge of the minimal expected concentration of the compound of interest in the environment, and judgment as to what constitutes a significant reduction in rate of diffusion. If the level of the free fraction inside the device becomes too high, the estimate of the time-integral of free concentrations obtained by use of this invention will be an underestimate. Thus while it may still be extremely useful, the estimate will not be a true time integral.

In the present embodiment of the invention preferred for measurement of the time integral of corticosterone in rats, the length of time over which the integration is performed is regulated so that the level of free corticosterone inside the implant does not exceed a value which would decrease the rate of diffusion by 10% at an environmental concentration of 5 nanograms/milliliter.

Use of other operating criteria, even including deliberate operation so as to obtain an underestimate, is not outside the novel concepts of this invention.

The differentially-permeable membrane used in the presently preferred embodiment of this invention is of a type well-known in the related arts, being standard cellulose dialysis membrane with a molecular weight cutoff of 12,000–14,000 daltons.

The choice of material for the differentially-permeable layer is a matter of convenience and may vary according to the application. The use of other types of cellulose membrane, of other synthetic or natural materials, and even of substantially intact membranes from organisms, is not outside the novel concepts of this invention.

As shown in FIGS. 1 and 3, the main compartment of the device is defined by rigid shell 12, which is covered in successive layers by membrane 13 and outer shell 14, which outer shell is plugged at one end by a cap 21.

At the opposite end of the outer shell 14, the means for exchanging the contents of the device is inserted, which means is shown in FIG. 1. The exchange means consists of tubes 17 and 18 fixed and sealed in plug 19, which tubes 17 and 18 project to open ends, respectively 17a and 18a, in the interior compartment 11, and also to open ends 17b and 18b in a septum block 20. The exchange means is inserted so that plug 19 seals within shell 12, sealing that end of the shell 12.

FIG. 2 shows the detailed construction of the septum block 20 with the tubes 17 and 18 flared at their ends, respectively 17b and 18b, and secured by means of a silicone rubber sheath 22 stretched tightly around wall members 26 within the septum block 20.

Silicone rubber sealer is placed at locations 27, 28, 29, and 30 providing at each location a seal member which provides or assures a leakproof seal and allows repeated penetration at locations 27 and 28 by needles, so that fluid introduced through a needle at 27 travels through tube 18 and inner compartment 11 before exiting through tube 17 and a needle inserted through body 28.

The material of the sheath 22 permits repeated puncturing.

Since the sealant bodies 27, 28, 29 and 30 effectively close the chambers 32 and 34, which respectively provide portions of the inlet and outlet passageways, the end openings 35 and 36 need not be closed.

It will readily be appreciated that if tubes 17 and 18 are externalized through the skin of an animal, having the device's assembled shells 12, 13, and 14 subcutaneously implanted and with the septum block 20 exposed in an easily-accessible position, then, by the procedure just described, the contents of the compartment 11 can be recovered with only minimal disturbance of the animal.

Components 14, 21, and 22 are silicone rubber in the presently preferred embodiment of the invention, while the other parts (excluding the cellulose dialysis membrane 13) are desirably of polyethylene. This choice of materials is well known in the prior art of implantable devices. However, construction of the device using other materials, or with some parts fused or made integral, is not to be regarded as outside the concepts of the present invention.

For example, simplified construction in which the walls of the device are made of a single homogeneous layer of material, which varies in thickness so as to provide some regions having higher permittivity, those regions thus taking on the functional character of diffusion ports, is within the concepts. Similarly, a construction having walls of uniform thickness and homogeneous composition may be given the desired functional properties by regionally applying a treatment which alters the permittivity of the material, as by enzymatically reducing the degree of crosslinking in a cellulose construction, thereby increasing its permittivity.

Similarly, the geometric form and arrangement of the diffusion ports can vary from that shown without departing from the novel concepts of the present invention so long as a distribution of the areas permittive of diffusion over the surface of the device is maintained.

Likewise, increasing or decreasing the surface area of the diffusion ports, which has the effect of regulating the rate at which the device accumulates the compound of interest, is entirely within the scope of the present invention. Likewise, use of such a device, which lacks the means for conveniently removing the fluid from the compartment without removing the device from the animal, is within the novel concepts of the present invention.

When the invention is practiced according to the method just described, it is found that the content of the compound of interest in the fluid recovered from the device, when measured by suitable means, is proportional to the time integral of the concentration of the free fraction of the substance of interest in the immediate environment of the device.

The constant of proportionality is determined by similarly practicing the invention, using as the environment of the device an artificially-prepared solution having known concentration of the free fraction of the compound of interest at all times, as will be apparent to one skilled in the art.

It will readily be appreciated that this invention, practiced according to the method and with the device just described, accomplishes these achievements previously specified: measurement of the time integral of a substance in a biological fluid, more particularly of the free fraction of that substance, the measurement being without necessity of the collection of blood, and by the final determination of the content of the substance in a single aliquot of fluid; that measurement being by a method and device which are adapted to repeated measurements within a single subject.

It will further be seen that the invention is adaptable to the measurement of any substance, for which both a binding preparation, and a material capable of acting as a membrane permitting diffusion of the free form but not the bound form of the substance, can be found.

Further, it will be seen that by use of a binding preparation of high capacity, the time interval over which the integration is accomplished can be extended over many hours or days, so long as the concentration of the free compound inside the device remains low, as previously discussed.

In addition, it will be recognized that the invention can be practiced so as to accomplish these objects with application to various biological fluids such as interstitial fluid, blood plasma, cerebrospinal fluid, lymph, etc., and also to fluids not contained within an organism, such as fluids produced by microbial fermentation or enzyme reaction in industrial processes.

Further it will be seen that the invention may be practiced with a device which has no parts external to the subject in which it is installed, so that while not optimally suited to repeated measurements within one subject, such a practice leaves the subject free of any external restraint or encumbrance.

Finally it will be seen that this invention is applicable in the measurement of the time integral of the concentration of substances without regard to their instantaneous concentrations, so that even though the instantaneous concentrations may be so low as to be unmeasurable by some known means, yet the integral of these concentrations over some time may be readily measurable by this same means.

3. Departures from prior and related art:

Perhaps the advantages and significant nature of the inventive concepts set forth herein may be realized by reference to recent advances in related art, which yet fail to accomplish the achievements in this invention. Cheesman, et al, (*Fertility and Sterility* 38:475, (1982)) have reported a method whereby a binding preparation is implanted in an animal, for the purpose of binding and sequestering a circulating hormone and depleting its concentration throughout the blood plasma of the animal. This art differs from the present invention in that the pathway, by which the hormone has access to the binding protein, has unknown and non-constant permittivity, so that no useful measurement can be obtained thereby.

Further, this related art is designed expressly to deplete and change the level of the hormone, and thereby to preclude useful measurement.

This present invention, quite in contrast, avoids depletion of, and allows measurement of, the time integrals of compounds such as hormones, by virtue of a pathway of precisely known constant, and limited permittivity.

Similarly, with regard to the device found useful in the practice of the invention, Goode (*British Journal of Pharmacology* 41:558, (1971)) has described a device somewhat superficially similar to that preferred in the present embodiment of this invention, but the Goode device is neither designed for, nor suitable for use, in the practice of this invention; for the Goode device incorporates a tubular reservoir, which communicates with its immediate environment through a single port of dialysis membrane installed at one end of the tubular reservoir, while at the other end two small tubes are fitted. Further, the Goode device is a subcutaneouslyimplanted reservoir for the chronic delivery of drugs, which operates by the diffusion of drugs from the reservoir, through the membrane, and into the surrounding environment. It is provided with externalized tubes for the purpose of replenishing the drugs contained in the reservoir.

Two prominent features which distinguish the device used in the presently preferred embodiment of this invention, from this related art, are first, the number and spatial arrangement of the diffusion ports, and second, the provision of a means of rapidly exchanging the contents of the device with minimal disturbance to the animal.

Each of these features is found to be essential in meeting the objects of the present invention. First, the dispersal of numerous diffusion ports over the lateral surface of the device is found to promote precisely reproducible rates of uptake of the substance of interest, while reliance upon a single port at the end of the device is found to give imprecise and non-reproducible results, presumably because of local depletion of the concentration of the substance of interest and unfavorable interactions with tissue in the case of the single-port device.

The innovation of using multiple dispersed ports of small size avoids the problem of local depletion, since the rate of uptake at each small port is quite low relative to the rate at which the affected volume of biological fluid equilibrates with its sources.

This same innovation insures that, although each small port individually may provide a rate of uptake higher or lower than average, due to tissue interactions, still the sum of the several rates will be much less variable than the rate of a single port, which is likewise liable to yield a rate either higher or lower than average in each installation.

This fact will be recognized to follow by analogy to the finding in the science of statistics, that the variance of the mean of $n$ observations drawn from a population, will be $\sigma^2/\sqrt{n}$, while the variance associated with each observation individually is $\sigma^2$.

As to the dispersion and number of the diffusion ports, it has been found that they should be of significantly scattered nature, i.e., that no more than one-half of the surface area of the port or ports is contained in a square region as small as one-tenth of the entire surface area of the wall means. This assures avoidance of local depletion (as discussed above) and assures a less-variable rate of uptake than with a single diffusion port. (The effect of the specification of a square region is to require, no matter what portion of the total area of the wall means is accounted for by ports, that the ports should be dispersed over a significant portion of the total area of the wall means, e.g., that even if the area of ports accounts for only 1/100 the area of the wall means, still no accident, which resulted in blockade of all the ports in a square area as large as 1/10 of the entire surface of the device, could reduce the available area of ports by more than one-half.)

Second, it is often important in practicing the present invention to avoid, so much as possible, the profound changes in the levels of substances which occur when the animal subject is handled or restrained. The innovation of providing the septum block, as a means for making connections necessary to service the implanted device quickly and without the necessity of restraining the animal, allows this object to be met.

With the device of the related art, immobilization of the animal is necessary in order for the practitioner to service the device; whereas, with the device of the presently preferred embodiment of this invention, immobilization is not practiced.

It is thus seen that a method and means for measurement of the time integral of concentration of chemical substances in biological fluids provides novel and advantageous concepts and features of operation and construction, including provision of a method permitting measurement of the time integrals of biologically effective concentrations of substances in the body fluids of unrestrained subjects, and provisions of a means including dispersed diffusion ports permitting maintenance of accurate rate of diffusion, and including a remote connector permitting rapid and convenient service of the measurement means.

Accordingly, it will be seen from the foregoing description of this invention according to this illustrative embodiment, considered with the accompanying drawings, that the present invention provides a new and useful method and means of time-integral measurement of chemical substances in biological fluids, having desired advantages and characteristics, and accomplishing its intended objects, including those hereinbefore pointed out and others which are inherent in the invention.

What is claimed is:

1. A method for determining the time integrals of the concentrations of chemical substances in a biological fluid, comprising:
   the step of exposing a composition, which is capable of binding the said chemical substances of interest to itself, to the biological fluid,
   said step of exposing being such that there is maintained a diffusion pathway of known and constant permittivity with respect to the chemical substances of interest for the duration of the measurement interval,
   this same diffusion pathway being such as to have negligible permittivity for the binding composition,
   said step of exposing also being such that the concentrations of those fractions of the chemical substances of interest which have traversed the diffusion pathway from the biological fluid to the binding composition, but which remain unbound by said binding composition, remain negligible relative to the concentrations of the chemical substances of interest available in the biological fluid for diffusion through said pathway,
   the method further comprising the step of quantitatively determining the amounts of the chemical substances of interest which have traversed the diffusion pathway during the interval of the exposure, the amounts of the chemical substances of interest traversing the diffusion pathway during the interval of the exposure thereby being proportional to the time integral of the concentrations of said substances in the biological fluid during said interval.

2. A method according to claim 1, in which the step of determining the amounts which have traversed the pathway includes the step of determining the amounts of the chemical substances of interest which are associated with the binding composition at the conclusion of the measurement interval.

3. A method for determining the time integral of the concentration of a chemical substance in a biological fluid, said method comprising:
   providing a binding composition capable of binding to itself a predetermined chemical substance in a biological fluid;
   providing a diffusion pathway of known and substantially constant permittivity with respect to said chemical substance, said diffusion pathway having negligible permittivity for said binding composition;
   exposing said binding composition to said biological fluid through said diffusion pathway so that said chemical substance in said biological fluid traversing said pathway is bound to said binding composition, with the duration of said exposure being such that the concentration of said chemical substance traversing said pathway and not thereafter bound by said binding composition is negligible; and
   determining from said binding composition the amount of said chemical substance bound thereto during the time interval of said exposure to thereby enable determination therefrom of the time integral of the concentration of said chemical substance in said biological fluid.

4. The method of claim 3 wherein said method includes providing substantially impermeable wall means defining a compartment for receiving and retaining said binding composition, providing port means in said wall means for establishing said diffusion pathway therethrough to said compartment, and positioning said wall means so that said port means is contiguous to said biological fluid to thereby allow said chemical substance to pass through said diffusion pathway to said compartment and be bound to said binding composition within said compartment.

5. The method of claim 4 wherein said step of providing said port means includes providing a plurality of spaced ports in said wall means, each of which ports provides a separate diffusion pathway to said compartment.

6. The method of claim 5 wherein said step of providing a plurality of spaced ports includes providing said ports so that no more than about one-half of the surface area of said ports is contained in a square region as small as one-tenth of the total surface of said wall means.

7. The method of claim 4 wherein said method also includes providing passageway means to said compartment spaced from said port means for enabling insertion of binding composition into said compartment and withdrawal of said binding composition from said compartment.

8. The method of claim 7 wherein said method includes inserting said binding composition into said compartment through said passageway means to start said exposure of said biological fluid to said binding composition, and later removing said binding composition from said compartment through said passageway means to terminate said exposure of said biological fluid to said binding composition.

9. The method of claim 7 wherein said method includes terminating said passageway means at a readily accessible location so that said binding composition can be inserted into and removed from said compartment while maintaining said wall means contiguous to said biological fluid.

* * * * *